United States Patent [19]

Pfeiffer et al.

[11] 4,395,391
[45] Jul. 26, 1983

[54] UNSYMMETRICALLY SUBSTITUTED DICARBOXYLIC-ACID-BIS-(2,4,6-TRIIODO-ANILIDES), THEIR PREPARATION, AND X-RAY CONTRAST MEDIA CONTAINING SAME

[75] Inventors: Heinrich Pfeiffer; Wolfgang Mützel; Ulrich Speck, all of Berlin, Fed. Rep. of Germany

[73] Assignee: Schering Aktiengesellschaft, Berlin, Fed. Rep. of Germany

[21] Appl. No.: 324,368

[22] Filed: Nov. 24, 1981

[30] Foreign Application Priority Data

Nov. 25, 1980 [DE] Fed. Rep. of Germany ....... 3044814

[51] Int. Cl.³ .................... A61K 49/04; C07C 101/68
[52] U.S. Cl. ........................................ 424/5; 562/442; 562/452; 562/456
[58] Field of Search ................. 424/5; 562/442, 443, 562/452, 456, 444

[56] References Cited

U.S. PATENT DOCUMENTS

| | | | |
|---|---|---|---|
| 3,637,825 | 1/1972 | Ackerman | 424/5 |
| 3,654,272 | 4/1972 | Felder et al. | 424/5 |
| 3,660,464 | 5/1972 | Bernstein et al. | 424/5 |
| 3,732,293 | 5/1973 | Ackerman | 424/5 |
| 3,770,820 | 11/1973 | Ackerman | 424/5 |
| 3,853,965 | 12/1974 | Ackerman | 424/5 |
| 3,939,204 | 2/1976 | Buttermann | 424/5 |
| 4,139,605 | 2/1979 | Felder | 424/5 |
| 4,225,577 | 9/1980 | Filly et al. | 424/5 |
| 4,264,572 | 4/1981 | Kleiger et al. | 424/5 |

*Primary Examiner*—James H. Reamer
*Attorney, Agent, or Firm*—Millen & White

[57] ABSTRACT

Unsymmetrically substituted dicarboxylic-acid-bis-(2,4,6-triiodo-anilides) of formula I

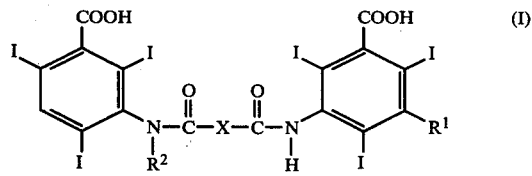

wherein
X is straight-chain or branched alkylene interrupted by one or more oxygen atoms,
$R^1$ is —NHacyl, —CH$_2$NHacyl, or —CONHR$^3$ wherein $R^3$ is hydrogen or a lower straight-chain or branched optionally mono- or poly-hydroxylated, alkyl residue, and where any hydroxyl groups present may be functionally modified, and
$R^2$ is hydrogen or lower alkyl, and their salts, are extraordinarily well suited, in view of their good pharmacological and physico-chemical properties, as water-soluble x-ray contrast media for all fields of application, in particular for i.v. cholegraphy and for computer tomography.

14 Claims, No Drawings

UNSYMMETRICALLY SUBSTITUTED DICARBOXYLIC-ACID-BIS-(2,4,6-TRIIODO-ANILIDES), THEIR PREPARATION, AND X-RAY CONTRAST MEDIA CONTAINING SAME

BACKGROUND OF THE INVENTION

The x-ray visualization of bile ducts and of the gall bladder requires contrast media which are excreted through the liver and gall bladder. All cholegraphics of clinical usefulness and which are to be administered intravenously are of the basis structure IV which was obtained for the first time in iodipamide (formula IVa). See German Pat. Nos. 936,928; 926,545; where for iodipamide IVa, $X=-(CH_2)_4-$.

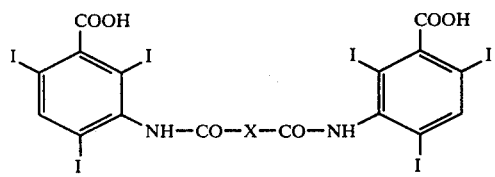

Their structural features are the following: 2 triiodinated anilines each with one free carboxyl group, with one hydrogen in the 5-position, and a dicarboxylic acid binding the two aromatic nuclei. To date, in conventional commercial cholegraphics, as regards variations in these structural features, the bridge member X has been varied on the one hand, and on the other hand, the hydrogen has been substituted in the 5- and 5'-positions.

Corresponding research using these and similar compounds (see also ROENTGENKONTRASTMITTEL by R. Barke, Georg Thieme publishers, Leipzig 1970, pp. 102—) has led to the observation that each of the structural elements assumes its own significance in the excretion through the gall bladder. In particular, the unsubstituted hydrogen atoms in the 5,5'-positions appear to be necessary for bonding to plasma albumins and transport proteins. Experience has shown that contrast media of formula IV which are substituted in the 5,5'-position by acylamino groups or aminocarbonyl groups may be somewhat more compatible, but much less of them passes through the bile duct; they are more markedly excreted through the kidney (see German Offenlegungsschriften Nos. 1 618 001 and 2 422 718).

SUMMARY OF THE INVENTION

Accordingly, it is an object of the present invention to provide new x-ray contrast substances which, in addition to passing well through the bile duct, also evince improved tolerability.

Upon further study of the specification and appended claims, further objects and advantages of this invention will become apparent to those skilled in the art.

These objects have been achieved by providing unsymmetrically substituted dicarboxylic-acid-bis-(2,4,6-triiodo-anilides) of the formula I

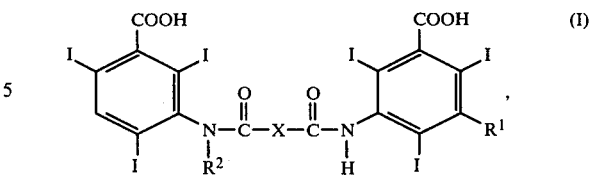

wherein
X is a straight chain or branched alkylene optionally interrupted by one or more oxygen atoms,
$R^1$ is —NHacyl, —CH$_2$NHacyl or —CONHR$^3$, wherein $R^3$ is hydrogen, or lower, straight chain or branched, optionally mono- or poly-hydroxylated alkyl, and any hydroxyl groups in
$R^1$ optionally may be functionally modified, and $R^2$ is hydrogen or lower alkyl, and the physiologically compatible salts thereof with inorganic or organic bases.

In another aspect, this invention provides a process for the preparation of these anilides as well as new contrast media containing compounds of formula I as the contrast producing substance.

DETAILED DISCUSSION

X, the straight-chain or branched-chain alkylene interrupted by one or more oxygen atoms, may contain from 1 to 12, preferably from 1 to 10 C atoms. Especially well suited is straight-chain alkylene of 1 to 8 C atoms which may be interrupted (i.e., the non-terminal positions can be occupied by O atoms) by 1 to 4, preferably 1 to 3 oxygen atoms. Illustratively, the following are examples: —CH$_2$—, —(CH$_2$)$_2$—, —(CH$_2$)$_3$—, —(CH$_2$)$_4$—, —(CH$_2$)$_6$—, —(CH$_2$)$_8$—, —CH$_2$—O—CH$_2$—, —(CH$_2$OCH$_2$)$_2$— and —(CH$_2$—O—CH$_2$)$_3$—. Suitable branched-chain residues X, for instance, include —HC(CH$_3$)—, —C(CH$_3$)$_2$—, —CH$_2$—CHCH$_3$—(CH$_2$)$_2$—, —CH$_2$—CHCH$_3$—CH$_2$— and the like.

When $R^1$ is —NHacyl or —CH$_2$NHacyl, the acyl group can be derived from an aliphatic hydrocarbon carboxylic acid of 2 to 4 C atoms, e.g., alkanoyl. Especially well suited are aliphatic carboxylic acid residues of 2 to 3 C atoms, for instance propionyl and preferably acetyl. Especially preferred are acyl residues which are substituted by 1 or 2 hydroxy groups, preferably by one hydroxy group, for instance, hydroxyacetyl and alpha-hydroxypropionyl.

$R^2$ as lower alkyl contains 1 to 4, preferably 1 to 3, and especially 1 to 2 C atoms. Illustrative examples in particular include methyl and ethyl, with methyl preferred.

When the alkyl residue $R^3$ is unsubstituted, it contains 1 to 4, preferably 1 to 3 and especially 1 to 2 C atoms. Methyl and ethyl are illustrative.

$R^3$ is mono- or a poly-hydroxyalkyl, it may also be straight-chain or branched. Preferable are alkyl groups of 2 to 5 C atoms, preferably 2 to 4 C atoms. The hydroxyl groups in the alkyl residue may be present in the form of primary and/or secondary and/or tertiary hydroxyl groups. The alkyl residue may contain 1 to 4, preferably 1 to 3 hydroxyl groups. Hydroxyethyl and 1,3-dihydroxy-propyl-(2) are illustrative.

When the hydroxy groups in the acyl residue and in the residue $R^3$ are present in functionally modified form, suitable resultant groups include ether groups, for instance ethoxy and methoxy; methoxy is preferred, i.e.

OH can be replaced by lower alkoxy, typically of 1 to 4 C atoms.

Where the compounds of formula I are to be used in the form of their physiologically compatible salts, both the conventional inorganic and organic bases known to the expert for such purposes are suitable. The salts are conventionally prepared by reacting the corresponding acids with the bases in a manner known per se.

Both metal salts, for instance the salts of sodium, calcium and magnesium and amine salts, for instance the salts of glucamine, N-methylglucamine, N,N-dimethylglucamine, ethanolamine, diethanolamine, morpholine among others, are suitable as physiologically compatible salts with bases. Basic aminoacids and aminoacid amides are also suitable for salt formation.

By providing the compounds of this invention wherein only one of the two 5,5',-position hydrogen atoms is substituted, new contrast-producing substances are obtained. These are significantly more hydrophilic and hence more compatible than their comparable parent compounds unsubstituted in the 5- and 5'-positions; nevertheless, they adequately bind to the plasma proteins and are excreted very predominantly through the gall bladder. This can be shown by comparing the values of protein binding, compatibility, biliary and renal excretion of the meglumine salts of the conventional agent iodipamide (B) and an agent of this invention, hexane-diacid-1-(3-carboxy-2,4,6-triiodo-anilide)-6-(3-carboxy-5-N-methyl-carbamoyl-2,4,6-triido-anilide) (A). Table 1.

TABLE 1

| Compound | A | B |
|---|---|---|
| distribution coefficient, butanol/water, pH 7.4 | 0.083 +/− 0.001 | 0.278 +/− 0.008 |
| protein bond to human serum at about 1.2 mg of iodine per ml | 43% | 77% |
| (1) LD$_{50}$, i.v., rat, (g of I/kg) | 5.5 | 2.6 |
| (2) rat, pericerebrally ED$_{50}$ (mg of I/kg) | 17.1 (11.8–23.6) | 6.35 (5.11–7.44) |
| (3) rat, intracisternal ED$_{50}$ (mg of I per kg) | 15.6 (11.5–21.1) | 1.07 (0.54–1.83) |
| (4) biliary excretion (% of dose) | | |
| up to 30 minutes | 61.3 +/− 7.8 | 59.4 +/− 3.6 |
| up to 3 h p. inj. | 85.9 +/− 3.0 | 91.5 +/− 2.3 |
| (5) renal excretion (% of dose) | | |
| up to 3 h p. inj. | 22.9 +/− 3.3 | 10.8 +/− 2.0 |

Notes for Table 1:
(1) The contrast media were injected in the form of meglumine salt solutions of 180 mg of iodine per ml at a rate of 0.8 ml/minute into male and female 100 g rats.
(2) Male and female rats of about 100 g in weight were injected intracerebrally between the cheekbone and the occiputal bone through a natural bone hole of the cranium while being slightly anesthesized with ether. 0.4 ml injections of contrast media solutions of various concentrations were used according to the method of Valzelli. The injection was carried out with a Hamilton syringe 710 N for which the penetration depth is limited to 10 mm. Depending on the preparation, at least 4 doses were tested on 10 animals. The effectiveness criteria used are the states of excitation, grave behavioral anomalies, coma and death over the period of 24 h.
(3) With the test equipment essentially the same ss in (2), 200–250 g rats are injected with contrast media in the cisterna suboccipitalis. The contrast media were diluted with a 3% mannite solution to adjust the osmotic pressure.
(4) Rats (of about 150 g) under ether anesthesia receive a polyethylene tubing in the ductus choledochus. About an hour after the animals awake from their anesthesia, the contrast media are injected intravenously in a dose of 60 mg I/kg and the bile is collected in fractionated manner until 3 h after the injection.
(5) Intact rats of about 100 g in weight receive 5 ml of water 20 minutes before administration of the contrast medium and thereupon in 1-hour intervals following administration of the test substances they receive orally 2 ml of water three times each. The urea was collected quantitatively until 3 h after the i.v. injection of the contrast medium in a dose of 60 mg of I/kg.
(4), (5) The contrast medium measurement was carried out either by means of the I$^{131}$ activity in the samples or, for non-radioactivity marked contrast media, using the x-ray fluorescence of iodine.

Surprisingly, the unsymmetrically substituted compounds of this invention, moreover, evince an extraordinarily marked enrichment in the liver parenchyma of test animals (dog and monkey), whereby the compounds of formula I are extremely well suited for computer tomography.

Computer tomography (CT) allows imaging sections through the living organism due to the varying absorption of x-rays in body fluids, organs and tissues. Unlike conventional radiology, a quantitative measurement of the x-rays is carried out and analyzed in CT. This method permits distinguishing between structures differing only very slightly in absorption.

Nevertheless, there are tissues and pathologically changed organs in the human body which lack sufficient absorption differences even for CT representation. In this regard, lesions such as tumors, metastases, etc., present in the liver parenchyma are a serious problem. It has been attempted to better distinguish between the pathological and healthy tissues of the parenchyma by administering contrast media containing iodine, just as in conventional radiology. In fact, in some cases, by administering a urographic agent, such distinction can be achieved. The differential enrichment of the contrast medium between the healthy and the pathological tissue however lasts only for a very short time and is weak because the contrast medium distributes itself only in an unspecific manner in the intravasal and the interstitial space of the liver. There might even be attenuations of naturally present differences in absorption of the tissues (A. W. Fuchs, P. Vock and M. Haertel: Pharmakokinetik intravasaler Kontrastmittel bei der Computer-Tomographie; Radiologe 19, 90–93, 1979).

While the use of bile contrast media to visualize the liver is obvious to try, it has failed, on the other hand, to result in any enrichment in the liver cells (K. H. Huebener: Computer-tomographische Densitometrie von Leber, Milz and Nieren bei intravenoes verabreichten lebergaengigen Kontrastmitteln in Bolusoform, Fortschr. Roentgenstr. 129, 289–307, 1978). Other researchers have intravenously administered particles in the form of emulsions, (J. L. Lamarque et al: The use of iodolipids in hepatosplenic computed tomography; J. Comput. Assist. Tomog, 3, 21–24, 1979), suspensions, (M. R. Violante, P. B. Dean: Improved Detectability of VX2 Carcinoma in the Rabbit Liver with Contrast Enhancement in Computed Tomography; Radiology 134, 237–239, 1980), or liposomes. A very satisfactory enhancement in density of such contrast media in the healthy liver parenchyma was obtained, and very good differentiation of the pathological tissue. However, the frequently high toxicity and/or the unreliable stability of the preparations is an impediment to routine clinical applications. To date, only iosefamic acid has been reported as a water-soluble contrast medium for enhancing the contrast of the liver parenchyma (R. E. Koehler, R. J. Stanley, R. G. Evans: Iosefamate meglumine: An Iodinated Contrast Agent for Hepatic Computed Tomography Scanning; Radiology 132, 115–118, 1979). Iosefamic acid results in a still adequate liver concentration for diagnosis improvement in the dog but unfortunately not in humans.

On the other hand, the new compounds of this invention, even during infusion of a relatively slight dosage of contrast media and for a relatively low blood level in dogs, show a strong enrichment of the contrast medium in the liver, such as is required by computer tomography. Moreover, the compounds of this invention provide aqueous salt solutions of high concentrations which can be heat-sterilized and are stable in long-term storage.

The extraordinarily pronounced enrichment of the compounds of this invention is shown in Table 2 listing the maximal enrichment in the liver following intravenous administration of the meglumine salt solutions of the prior art iosefamic acid (D) and of a compound of this invention, 3-oxapentane-diacid-1-(2-carboxy-2,4,6-triiodo-N-methylanilide)-5-(3-carboxy-5-N-methylcarbamoyl-2,4,6-triiodo-anilide) (E).

TABLE 2

| COMPOUND | Maximum enrichment in dog liver | |
|---|---|---|
| | 360 mg I/kg EMI units | min. p. appl. |
| D | 22.8 | 80 |
| E | 42.1 | 90 |

The values were obtained from healthy male and female beagles (Schering, breeder) with weights of 9–14 kg. The meglumine salt solutions contained 180 mg of I/ml.

The investigation of the x-ray density of the liver before administration of the contrast media and every 5 minutes up to 90 minutes thereafter was carried out using a full-body scanner of the EMI CT 5005/12 type, which operates on the basis of the rotation-translation principle. The scanning time was 20 seconds, the tube voltage 120 kv. For an image matrix of $320 \times 320$ elements, the standard deviation from the mean value of a normalized water phantom was 1.6% (i.e., $+/-8$ EU=EMI units). The computer tomograms were analyzed always on the same liver area by means of the analyzer "IVC" of the EMI Co.

Not only are the compounds of this invention suitable for cholegraphy and computer tomography, but they are also fundamentally suited as contrast-producing substances in various fields of application for water-soluble x-ray contrast media, in particular to visualize body cavities and also, for instance, to show the by-passing urinary passages of the stomach-intestinal canal, the hollows of the joints, the tracheobronchial system, etc. and also for histerosalpingography.

In all cases, the new contrast media of this invention provide particularly good detail in the structures shown. Their administration is fully conventional, unless indicated otherwise herein, and is analogous to known agents such as those discussed above.

The invention therefore also concerns new contrast media based on the compounds of this invention.

The preparation of the new contrast media based on the compounds of this invention can be carried out by methods known per se, for instance by processing the contrast-producing substance into a suitable form using medically conventional additives such as stabilizers like sodium edetate, calcium-di-sodium-edetate, physiologically compatible buffers such as tromethamine buffer, among others, for intravenous application. The concentration of the new contrast media in an aqueous medium depends on the particular x-ray method being used for diagnosis. The preferred concentrations and dosages of the new compounds are in the range of 50–400 mg I/ml for concentration and 5–500 ml for dosages. Concentrations of 100 to 400 mg I/ml are especially preferred.

One process for preparing the new compounds of formula I comprises conventionally reacting a compound of formula II

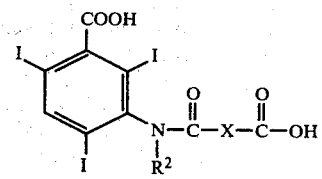

where $R^2$ and X are as defined above, with a chlorinating reagent and a tri-iodinated aminobenzoic acid of formula III, (where $R^1$ is defined as above):

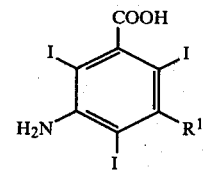

The amidation reaction is carried out in a suitable polar solvent such as dioxane, dimethylformamide or dimethyl acetamide or their mixtures, in manner known per se. For example, a compound of formula II is first reacted at 0° to 40° C., preferably 0° to 20° C. with a chlorinating reagent to form an acid chloride of formula V

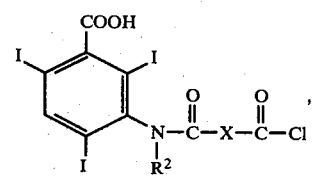

where $R^2$ and X are as defined above. Without isolation, this is reacted with a compound of formula III at a temperature of 0° to 80° C., preferably 20° to 40° C., to form the compounds of this invention of formula I.

Suitable chlorinating reagents for instance include phosphorus pentachloride oxalylchloride, phosgene or 1,1-dichloro-methylmethylene ether, preferably thionyl chloride.

After the reaction is completed, the compound of formula I is isolated by water precipitation and purified by methods known to the expert, e.g., by salt formation using a suitable inorganic or organic base such as ammonia or an amine or alkali metal hydroxide.

The intermediary protection of free hydroxyl groups is accomplished by conventional methods using protective groups which can easily be split off again. The introduction of such groups can be implemented by acylation (for instance, introducing a preferred acetyl residue or benzoyl residue), by etherification (for instance, by introducing the triphenylmethyl residue), or by acetalization or ketalization for instance using acetaldehyde, dihydropyran, acetone or 2,2-dimethoxypropane.

The subsequent splitting-off of the intermediarily introduced protective groups to free the hydroxyl groups desired in the end, also takes place by methods known to the expert. Thus the splitting-off of the protective groups can take place in the absence of a special reaction stage and with the reprocessing and isolation of the reaction products. The splitting-off, however, can also take place in conventional manner in a separate reaction stage. Protective acetal, ketal or ether groups, for instance, can be split off using acid hydrolysis.

The conversion of the compounds of this invention of formula I into their physiologically compatible salts using conventional inorganic or organic bases known to the expert also is carried out by well known methods.

The new carboxylic acids of formula II used in the process can be readily obtained by methods known per se by reacting the known corresponding 3-amino- or 3-lower-alkylamino-2,4,6-triiodo-benzoic-acid with an aliphatic dicarboxylic acid of the formula HOOC—X—COOH in the form of its cyclic anhydride

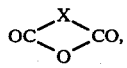

its dicarboxylic-acid-dichloride ClCO—X—COCl or its lower-alkyl-ester-chloride ClCO—X—CO—O—(lower-alkyl), where X is defined as above.

If the dicarboxylic acid HOOC—X—COOH is used in the form of its cyclic anhydride, the reaction preferably is carried out at a temperature of 80° to 120° C., preferably at 100° C., in a polar solvent such as dimethylformamide, hexamethyl-phosphoric-acid-triamide, preferably in dimethylacetamide, in the presence of an acid such as sulfuric acid, phosphoric acid, preferably p-toluene-sulfonic acid.

After the reaction, the raw product is extracted by water precipitation and is purified by means of salt formation using a base such as potassium or sodium hydroxide, preferably ammonia. Then the acid of formula II is freed again by acidification with a mineral acid such as hydrochloric acid as exemplified and explained in closer detail in the following example.

Diglycolic-acid-mono-3-carboxy-2,4,6-triiodo-N-methyl-anilide

A solution of 952 g (1.8 moles) of 3-methylamino-2,4,6-triiodo-benzoic acid in 1.8 liter of dimethylacetamide is reacted with 418 g (3.6 moles) of diglycolic-acid anhydride and 90 g of p-toluene sulfonic acid and heated in the steam bath with stirring for 7 h. After stirring overnight at room temperature, the dark-brown solution is extensively evaporated in vacuum. The viscous-fluid residue is introduced into 18 liters of water, stirred overnight, ground in the mortar and thoroughly stirred in 9 liters of fresh water for about one hour. The precipitate is evacuated and dried in vacuum at 50° C. The raw product (1,043 g) is dissolved in 5.2 liters of ethanol, filtered until clean, reacted with 274 ml in 13 N ammonia and stirred overnight at room temperature. After cooling in ice, the crystallized salt is evacuated, dissolved in 10 liters of water, stirred with 100 g of charcoal, filtered and acidified with 356 ml of 12 N hydrochloric acid. The initially smudgy precipitate is slowly transformed (after vaccination). After stirring over the weekend, the precipitate is evacuated, stirred to completion for 1 h in 4.5 liters of water, evacuated, and dried in vacuum at 50° C. The yield of the title compound is 730.3 g (62.9% of theoretical); m.p.: 177°/179°-181° C.; iodine per computation=59.0%; measured=59.0%.

If the dicarboxylic acid HOOC—X—COOH is reacted in the form of its dichloride with 3-amino- or 3-lower-alkylamino-2,4,6-triiodo-benzoic acid, then the reaction is carried out between 0° C. and room temperature, preferably at 0° C., in a polar solvent such as dimethylformamide, dioxane, preferably in dimethylacetamide. After completion of the reaction, first the acid chloride of formula IIa

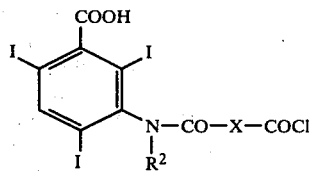

is obtained. This is hydrolyzed by treatment with an aqueous alkali metal hydroxide, preferably sodium hydroxide.

By adding a mineral acid, preferably hydrochloric acid, to the alkali metal salt so obtained, the carboxylic acid of formula II will be released. Thereupon, it is separated on the basis of differential solubilities from the dicarboxylic-acid-bis-anilide of formula IIb generated as a byproduct

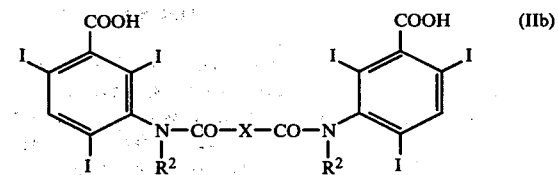

This preparation procedure is explained in closer detail in the following example.

3,6,9-tri-oxaundecane-diacid-mono-3-carboxy-2,4,6-triiodo-anilide 82 ml (400 millimoles) of 3,6,9-trioxaundecane-diacid-chloride are dissolved with ice cooling in 100 ml of dimethylacetamide. A solution of 51.5 g (100 millimoles) of water-free 3-amino, 2,4,6-triiodo-benzoic acid in 200 ml of dimethylacetamide is rapidly placed with ice cooling into the above solution. The ice bath is removed after 10 minutes and the solution is stirred at room temperature for 48 h. Then the solvent is extensively distilled off in vacuum and the oily residue in 1 liter of water is reacted while being ice-cooled with 152 ml of 11 N soda lye. After 16 h, the solution is thoroughly stirred with 10 g of charcoal, filtered, diluted with 8.5 liters of water and acidified with 175 ml of 12 N hydrochloric acid. The corresponding diacid-bis-anilide generated as a byproduct (about 12 g) is precipitated and evacuated. The filtrate is evaporated in vacuum to about 600 ml, a precipitate being obtained. This precipitate is evacuated, finely ground in 100 ml of water in the mortar, stirred for one hour evacuated and dried.

Yield: 54.0 g (75.1% of theoretical) of the title compound. M.p.: 109°-113° C. Iodine, computed=53.0%; measured=52.7%.

If a dicarboxylic acid HOOC—X—COOH in the form of its lower-alkyl-ester chloride ClCO—X—COO—(lower alkyl) is used for the preparation of the carboxylic acid II, then it will be reacted at a temperature between 20° and 80° C., preferably at 50° C., in a polar solvent such as dimethylformamide, hexamethyl-phosphoric-acid-triamide, preferably in dimethylacetamide, with 3-amino- or 3-N-lower-alkylamino-2,4,6-triiodo-benzoic acid. Firstly, the monoester IIc is obtained by water precipitation,

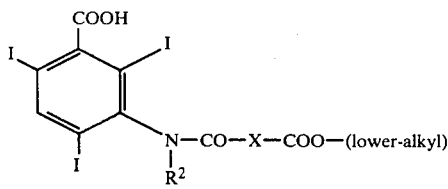

(IIc)

This is saponified by treatment with an alkali metal hydroxide in water in a dissolution-intermediary, preferably dioxane, at 60° to 110° C., preferably at 90° C. An acid of formula II is obtained, and is purified by salt-formation as explained in further detail in the illustrative preparations below:

Glutaric-acid-mono-3-carboxy-2,4,6-triiodo-N-methyl-anilide 9.95 ml (72 millimoles) of gluteric-acid monomethylester chloride is dripped with stirring within 5 minutes into a mixture of 15.9 g (30 millimoles) of 3-N-methylamino-2,4,6-triiodo-benzoic-acid in 36 ml of dimethylacetamide (heat of reaction). After stirring overnight, the solution is reacted with 150 ml of water and left to stand overnight. The grease-like substance is separated, washed once with water, reacted with 100 ml of dioxane and with 100 ml of water, heated with stirring to 85° C. and kept at a pH of 9 by batch-wise addition of 11 N soda lye (about 7.5 ml) over a period of 45 minutes. Then the dioxane is distilled off in vacuum, the aqueous solution is diluted to 150 ml and acidified by means of 8.25 ml of 12 N hydrochloric acid while stirring. After several hours, the precipitate is evacuated, thoroughly stirred into 100 ml of water, evacuated and dried.

Yield: 14.6 g (75.6% of theoretical) of the title compound; m.p. is 238°-239° C.

In a similar manner, there is obtained glutaric-acid-mono-3-carboxy-2,4,6-triiodo-anilide by reacting glutaric-acid-monomethylester chloride with 3-amino,2,4,6-triiodo-benzoic-acid and by crystallizing the final product out of acetic acid.

Yield: 14.5 g (76.9% of theoretical); m.p.: 227°-230° C.

Adipic-acid-mono-3-carboxy-2,4,6-triiodo-N-methyl-anilide 112 ml (720 millimoles) of adipic-acid-monomethylester chloride is dripped within 15 minutes into a solution of 158.7 g (300 millimoles) of 3-methylamino-2,4,6-triiodo-benzoic-acid in 360 ml of dimethylacetamide and with slight cooling (maximum inner temperature 50° C.). After stirring overnight at room temperature, the mixture is introduced into 1.5 liters of water and decanted from the separated grease-like substance. The grease-like substance in 1.5 liters of dioxane and 1.5 liters of water is reacted batchwise with 11 N soda lye (a total of 100 ml) for 45 minutes in the steam bath while stirring for the purpose of saponification until the pH value no longer drops below 9. The dioxane is distilled off in vacuum, the residual solution is diluted with water to a volume of 1.5 liters, and acidified with 100 ml of 12 N hydrochloric acid. The grease-like precipitate is ground in fresh water in a mortar until largely solidifying. This raw product is dissolved in 1.8 liters of methanol by adding 48 ml of 13 N ammonia, treated with 18 g of charcoal, filtered, reacted with 1.8 liters of water, freed of methanol in vacuum and acidified with 100 ml of 12 N hydrochloric acid. After stirring overnight, the precipitate is ground under fresh water in the mortar until it is wholly solidified.

Yield: 170.9 g (86.7% of theoretical) of the title compound: m.p.=224°-226° C.

Sebacic-acid-mono-2,4,6-triiodo-3-carboxy-N-methyl-anilide

The solution of 158.7 g (300 millimoles) of 3-methylamino-2,4,6-triiodo-benzoic acid in 360 ml of dimethylacetamide is reacted with stirring and cooling (inside temperature a maximum of 50° C.) within 15 minutes with 169 g (720 millimoles) of sebacic-acid-monomethylester chloride. After stirring overnight, the solution is reacted with 150 ml of water and again is left to stand overnight at room temperature. The grease-like substance is dissolved in 1.5 liters of dichloroethane while being heated on the steam bath, is shaken out several times with water and then evaporated until dry. This residue is boiled three times with 1 liter of hexane in each case to remove the sebacic-acid monomethylester; then it is reacted each time with 600 ml of dioxane and water, heated while being stirred to 85° C. and saponified for 45 minutes by the batch-wise addition of 11 N soda lye (about 70 ml) at a pH of 9. Next, the dioxane is distilled off in vacuum, the aqueous solution is diluted to 1.5 liters and acidified with 90 ml of 12 N hydrochloric acid. The precipitated grease-like substance is kneaded with water several times until it solidifies.

Yield: 209 g (97.7% of theoretical) of the title compound. M.p.: 157°-164° C.

Sebacic-acid-mono-2,4,6-triiodo-3-carboxy-anilide is obtained in similar manner by reacting 154.4 g (300 millimoles) of 3-amino-2,4,6-triiodo-benzoic acid in 360 ml of dimethylacetamide while stirring and cooling with 269 g (720 millimoles) of sebacic-acid-monomethylester chloride, by precipitating with water, by saponifying by means of dichloroethane and hexane and in dioxane/water.

Yield: 181 g (86.3% of theoretical); M.P.: 189°-193° C.

The aniline compounds used in the process and of formula III with $R^1$ as defined above are generally known including when $R^3$ denotes hydrogen or a straight-chain or a branched lower alkyl residue. Aniline compounds of formula III where $R^3$ denotes a lower straight-chain or branched mono- or polyhydroxylated alkyl residue ($R^{3'}$) with any present hydroxyl groups possibly being functionally protected, are prepared by methods known per se, for instance by reacting 3-lower-alkoxy-carbonyl-5-nitro-benzoic acid with an amine of the formula $R^{3'}-NH_2$ at 40° to 80° C., preferably at 60° C., by aminolysis, to form the corresponding 3-($NR^{3'}$-carbamoyl)-5-nitro-benzoic acid. By hydrogenating this compound thereafter in known manner and by iodinating in a manner known to the expert the 3-($NR^{3'}$-carbamoyl)-5-amino-benzoic acid is connected into 3-($NR^3$-carbamoyl)-5-amino-2,4,6-triiodo-benzoic acid, as explained in further detail in the following example.

5-amino-N-(2-methoxyethyl)-2,4,6-triiodo-isophthalamic acid (1) 239.2 g (1 mole) of 5-nitroisophthalamic-acid-monoethylester is dissolved in 444 ml (5 moles) of 2-methoxyethylamine, the temperature rising to 60° C. After stirring for 2 days at room temperature, the mixture is evaporated in vacuum at 70° C., dissolved with 2.4 liters of water, adjusted to a pH of 7 by means of hydrochloric acid, treated with charcoal and then acidified to a pH of 1 with 12 N hydrochloric acid. The precipitate provides 217.6 g (81.1% of theoretical) of 5-nitro-N-(2-methoxyethyl)-isophthalamic acid; m.p.=203°–207° C.

(2) A solution of 89 g (0.33 moles) of the above nitro compound in 0.7 liters of water and 185 ml of 2 N ammonia receives 7 g of Raney nickel catalyst and is hydrogenated with hydrogen at 50 atm. initial pressure. Then the filtered solution is diluted to 1.7 liters and dripped within 150 minutes into a warm solution at 70°–80° C. of 1.7 moles of iodine chloride in 4 liters of 1.5 N hydrochloric acid. After two more hours, the mixture is left to cool overnight, the precipitate is evacuated, and the substance is thoroughly stirred with water.

Yield: 147 g (71.5% of theoretical) of the title compound; m.p.=234°–238° C. (decomposition).

Without further elaboration, it is believed that on skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

3-oxapentane-diacid-1-(3-carboxy-2,4,6-triiodo-N-methylanilide)-5-(3-acetamido-5-carboxy-2,4,6-triiodo-anilide)

In the presence of ice cooling, 55.8 ml (770 millimoles) of thionyl chloride is dripped for 60 minutes into a solution of 225.7 g (350 millimoles) of diglycolicacid-mono-3-carboxy-2,4,6-triiodo-N-methylanilide in 700 ml of dimethylacetamide. The ice bath is removed after 10 minutes and the solution is stirred overnight at room temperature. Thereupon, 196 g (343 millimoles) of 3-amino-5-acetamido-2,4,6-triiodo-benzoic acid is introduced; there is heat of reaction up to +40° C. After two more days, the solution is stirred into 3.5 liters of water; the precipitate so resulting is treated with fresh water, evacuated and dried. The raw product (409 g) is dissolved with 2 liters of ethanol, filtered, and reacted with 141 ml (717 millimoles) of dicylcohexylamine. After stirring overnight and after cooling in ice, the crystalline salt is evacuated and washed with a little ethanol; 245 g (46% of theoretical) is obtained. This salt is suspended in 2.4 liters of water and reacted with 50 ml of 11 N soda lye. The dicyclohexylamine separating from the cloudy solution is removed, the solution is filtered through a folded filter, treated with 24 g of charcoal, filtered and acidified with 105 ml of 12 N hydrochloric acid. After stirring overnight, the precipitate is evacuated, stirring thoroughly with 1.2 liters of water for about one hour, evacuated and dried in vacuum at 50° C.

Yield: 175.1 g (42.6% of theoretical) of the title compound. M.p.=261°–263° C. (decomposition). Iodine, computed=63.5%; measured=63.05%.

EXAMPLE 2

3-oxapentane-diacid-1-(3-carboxy-2,4,6-triiodo-N-methylanilide)-5-(3-carboxy-5-N-methylcarbamoyl-2,4,6-triiodo-anilide)

55.8 ml (770 millimoles) of thionyl chloride is dripped with ice cooling in 40 minutes into a solution of 225.7 g (350 millimoles) of diglycolic-acid-mono-3-carboxy-2,4,6-triiodo-N-methylanilide in 700 ml of dimethylacetamide. The ice bath is removed after 10 minutes and the solution is stirred overnight at room temperature. Thereupon, 196 g (343 millimoles) of 2,4,6-triiodo-5-amino-isophthalic-acid-monomethylamide is introduced. There is heat of reaction up to +35° C. The next day the solution is stirred into 3.5 liters of water and the precipitate is evacuated some time later; it is then thoroughly stirred into 1.75 liters of water, evacuated and dried in vacuum at 50° C. The raw product (572 g) is dissolved by means of 2 liters of ethanol, filtered and reacted with 182 ml (926 millimoles) of dicyclohexylamine. After stirring overnight and cooling in ice, the crystalline salt is evacuated and after-washed with a little ethanol. Then the salt is suspended in 4 liters of ethanol and reacted with 126 ml of 11 N soda lye, the dicyclohexylamine precipitating. After this separation, the solution is filtered, treated with charcoal and acidified with 255 ml of 12 N hydrochloride. The precipitate is thoroughly stirred with water, evacuated and dried.

Yield: 291.3 g (70% of theoretical) of the title compound. M.p.=271°–273° C. (decomposition). Iodine, computed=59.0%; measured=58.4%.

EXAMPLE 3

3-oxapentane-diacid-1-(3-carboxy-2,4,6-triiodo-N-methylanilide)-5-(3-carboxy-5-ethylcarbamoyl-2,4,6-triiodo-anilide)

Similarly to example 2, a solution of 225.7 g (350 millimoles) of diglycolic-acid-mono-3-carboxy-2,4,6-triiodo-N-methylanilide in 700 ml of dimethylacetamide is sequentially reacted with 55.8 ml (770 millimoles) of thionyl chloride and 201 g (343 millimoles) of 5-amino-N-ethyl-2,4,6-triiodo-isophthalamic-acid; upon completion of the reaction, 3.5 liters of water is stirred in. The precipitate is evacuated, thoroughly stirred with water, evacuated and dried. This raw product (487 g) is suspended in 4.2 liters of water and dissolved by adding 72 ml of 13 N ammonia, treated with 42 g of charcoal and acidified with 94 ml of 12 N hydrochloric acid. The precipitate is evacuated, thoroughly stirred in water and dried.

Yield: 337.1 g (81.0% of theoretical) of the title compound. M.p.=240°–243° C. (decomposition). Iodine, computed=62.8%; measured=63.0%.

EXAMPLE 4

3-oxapentane-diacid-1-(3-carboxy-2,4,6-triiodo-N-methylanilide)-5-(3-carboxy-5-[2-methoxyethylcarbamoyl]-2,4,6-triiodo-anilide)

Similarly to example 2, a solution of 225.7 g (350 millimoles) of diglycolic-acid-mono-3-carboxy-2,4,6-triiodo-N-methylanilide in 700 ml of dimethylacetamide is sequentially reacted with 55.8 ml (770 millimoles) of thionyl chloride and 211 g (343 millimoles) of 5-amino-N-(2-methoxyethyl)-2,4,6-triiodo-isophthalamic acid and stirred into 3.5 liters of water. The precipitate is evacuated, stirred thoroughly with water, evacuated and dried. The raw product (483.5 g) is suspended in 4.2 liters of water and dissolved by adding 72 ml of 13 N ammonia, treated with 40 g of charcoal, and acidified with 94 ml of 12 N hydrochloric acid. The precipitate is evacuated, thoroughly stirred with water, evacuated and dried.

Yield: 339.8 g (79.7% of theoretical) of the title compound. M.p.=240°-247° C. (decomposition). Iodine, computed=61.3%; measured=61.0%.

EXAMPLE 5

3-oxapentane-diacid-1-(3-carboxy-2,4,6-triiodo-N-methylanilide)-5-(3-carboxy-5-acetamidomethyl-2,4,6-triiodo-anilide)

Similarly to example 1, a solution of 6.45 g (10 millimoles) of diglycolic-acid-mono-3-carboxy-2,4,6-triiodo-N-methylanilide in 20 ml of dimethylacetamide is sequentially reacted with 1.6 ml (22 millimoles) of thionylchloride and 5.86 g (10 millimoles) of 2,4,6-triiodo-3-amino-5-acetamidomethyl-benzoic-acid, stirred for 7 days at room temperature and then stirred into 100 ml of water. The precipitate is evacuated, dried (12.3 g) and crystallized out of acetic acid.

Yield: 7.9 g (65% of theoretical) of the title compound. M.p.=231°-238° C. (decomposition). Iodine, computed=62.8%; measured=61.9%.

EXAMPLE 6

3,6,9-tri-oxaundecane-diacid-1-(3-carboxy-2,4,6-triiodo-anilide)-11-(3-carboxy-5-methylcarbamoyl-2,4,6-triiodo-anilide)

16 ml (200 millimoles) of thionyl chloride is dripped with ice cooling into a solution of 71.9 g (100 millimoles) of 3,6,9-trioxaundecane-diacid-mono-3-carboxy-2,4,6-triiodo-anilide in 200 ml of dimethylacetamide. After stirring for 6 hours at room temperature, this mixture is reacted with 57.2 g (100 millimoles) of 5-amino-2,4,6-triiodo-isophthalic-acid-monomethylamide, stirred for another 70 hours and lastly is stirred into 1 liter of water. After stirring for 20 hours, the solidified precipitate is evacuated, washed with water and dried. This raw product (156 g) is dissolved in 636 ml of ethanol with addition of 54 ml of dicyclohexylamine. After stirring overnight and cooling in ice, the crystallized salt is evacuated, washed with ethanol on a frit, suspended in 1.4 liters of water and reacted with 37 ml of 11 N soda lye. The dicyclohexylamine is separated, the aqueous solution is filtered, treated with 14 g of charcoal, and acidified with 75 ml of 12 N hydrochloric acid. The precipitate thoroughly stirred with water provides 104 g (81.5% of theoretical) of the title compound with a m.p. of 199°-205° C.; iodine, computed=59.8%, measured=59.0%.

EXAMPLE 7

3,6,9-trioxaundecane-diacid-1-(3-carboxy-2,4,6-triiodo-anilide)-11-(5-acetamido-3-carboxy-2,4,6-triiodo-anilide)

Similarly to example 6, a solution of 71.9 g (100 millimoles) of 3,6,9-trioxaundecane-diacid-mono-3-carboxy-2,4,6-triiodo-anilide in 200 ml of dimethylacetamide is sequentially reacted with 16 ml (220 millimoles) of thionyl chloride and 56.06 g (98 millimoles) of 3-amino-5-acetamido-2,4,6-triiodo-benzoic acid, and after another 48 hours is stirred into 1 liter of water, a precipitate then being formed. This precipitate is washed with water, dried, dissolved in 950 ml of ethanol and reacted with 43 ml (220 millimoles) of dicyclohexylamine, a precipitated then being generated. The precipitate is abruptly evacuated, suspended in 1.3 liters of water, and while stirred, is reacted with 30 ml of 11 N soda lye, whereupon the dicyclohexylamine is separated, the aqueous solution is filtered, treated with 13 g of charcoal and acidified with 60 ml of 12 N hydrochloric acid.

Yield: 87.9 g (69.1% of theoretical). M.p.=240°-248° C. (decomposition). Iodine, computed=59.8%; measured=59.4%.

EXAMPLE 8

Glutaric-acid-1-(3-carboxy-2,4,6-triiodo-N-methylanilide)-5-(3-carboxy-5-N-methylcarbamoyl-2,4,6-triiodo-anilide)

A solution of 128.6 g (200 millimoles) of glutaric-acid-mono-3-carboxy-2,4,6-triiodo-N-methyl-anilide in 400 ml of dimethylacetamide is reacted while being ice-cooled with 31.9 ml (440 millimoles) of thionyl chloride and after stirring overnight at room temperature with 112.1 g (196 millimoles) of 2,4,6-triiodo-5-amino-isophthalic-acid-mono-methylamide. After stirring overnight, the solution is introduced into 2 liters of water. The precipitate so generated is evacuated and dried. This raw product (248 g) is dissolved in 2.3 liters of water by adding 33 ml of 13 N ammonia, is treated with 23 g of charcoal, and precipitated by adding 50 ml of 12 N hydrochloric acid. The precipitate is evacuated, stirred thoroughly in 2 liters of 1 N hydrochloric acid and water, briskly evacuated and dried in vacuum at 60° C. in air flow.

Yield: 191.5 g (81.3% of theoretical) of the compound of the invention. M.p.=257°-261° C. (decomposition). Iodine, computed=68.6%; measured 63.1%.

EXAMPLE 9

Hexane-diacid-1-(3-carboxy-2,4,6-triiodo-N-methylanilide)-6-(3-carboxy-5-N-methylcarbamoyl-2,4,6-triiodo-anilide)

A solution of 13.1 g (20 millimoles) of adipic-acid-mono-3-carboxy-2,4,6-triiodo-N-methylanilide in 40 ml of dimethylacetamide while being ice-cooled is reacted with 3.2 ml (44 millimoles) of thionyl chloride and, after stirring overnight at room temperature, with 11.2 g (19.6 millimoles) of 2,4,6-triiodo-5-amino-isophthalic-acid-monomethylamide. After stirring overnight, this solution is stirred into 200 ml of water, with a precipitate being generated. This precipitate while still moist is dissolved in 120 ml of ethanol, reacted with 9.4 ml (48 millimoles) of dicyclohexylamine and stirred overnight. The separated salt is evacuated, suspended in 250 ml of water and reacted with 6.5 ml of 11 N soda lye. The dicyclohexylamine which separates is removed. The aqueous solution is filtered, treated with charcoal, and acidified with 13 ml of 12 N hydrochloric acid. After stirring overnight, the precipitate is evacuated, washed and dried.

Yield: 18.1 g (91.6% of theoretical) of the title compound. M.p.=240°-247° C. (decomposition). Iodine, computed=62.9%; measured=62.2%.

EXAMPLE 10

Hexane-diacid-1-(3-carboxy-2,4,6-triiodo-anilide)-6-(3-carboxy-5-N-methylcarbamoyl-2,4,6-triiodo-anilide)

A solution of 128.6 g (200 millimoles) of adipic-acid-mono-2,4,6-triiodo-3-carboxy-anilide in 400 ml of dimethylacetamide while being ice-cooled is reacted with 31.9 ml (440 millimoles) of thionyl chloride and after stirring overnight at room temperature with 112.1 g (196 millimoles) of 2,4,6-triiodo-5-amino-isophthalic-acid-monomethylamide. There is a heat of reaction up to about 35° C. After stirring overnight, the solution is introduced in 2 liters of water, with a precipitate being formed. While still moist, this precipitate is dissolved in 2.4 liters of methanol and by adding 33 ml of 13 N ammonia is adjusted to a pH of 7.5, then treated with 23 g of charcoal, diluted with 2.4 liters of water and again treated with 23 g of charcoal, evaporated down to 2 liters and acidified with 50 ml of 12 N hydrochloric acid. The precipitate is evacuated some time later, thoroughly stirred in 2 liters of 1 N hydrochloric acid, briskly evacuated and dried in vacuum at 60° C. and in air flow.

Yield: 184.2 g (78.5% of theoretical) of the title compound. M.P.=270°-282° C. (decomposition). Iodine, computed=63.6%; measured=64.1%.

EXAMPLE 11

Preparing a ready-to-use meglumine salt solution with a concentration of 300 mg I/ml:

| | |
|---|---|
| 3-oxapentane-diacid-1-(3-carboxy-2,4,6-triiodo-N—methylanilide)-5-(3-carboxy-5-N—methylcarbamoyl-2,4,6-triiodo-anilide) | 472.3 g |
| N—methylglucamine | 153.8 g |
| calcium sodium edetate | 0.1 g |
| aqua bidestillata   to make | 1000 ml |

The edetate, the iodine compound and lastly as much meglumine is placed into about 5.50 ml of ready aqua bidestillata to achieve a pH value of 7.0+/−0.5. Then the solution is filled to 1000 ml using aqua bidestillata, and bottles or ampules are filled in turn and sterilized at 120° C.

EXAMPLE 12

Preparing a ready-to-use methyl-glucamine-salt solution with a concentration of 180 mg I/ml.

| | |
|---|---|
| 3,6,9-trioxaundecane-diacid-1-(3-carboxy-2,4,6-triiodo-anilide)-11-(acetamido-3-carboxy-2,4,6-triiodo-anilide) | 300.9 g |
| N—methylglucamine | 92.3 g |
| calcium sodium edetate | 0.1 g |
| aqua bidestillata    to make | 1000 ml |

The solution is prepared as in example 11, filled into containers and sterilized.

EXAMPLE 13

Decane-diacid-1-(3-carboxy-2,4,6-triiodo-N-methylanilide)-10-(3-carboxy-5-N-methylcarbamoyl-2,4,6-triiodo-anilide)

3.2 ml (44 millimoles) of thionyl chloride is dripped within 5 minutes and with ice cooling into a solution of 14.3 g (20 millimoles) of sebacic-acid-mono-2,4,6-triiodo-3-carboxy-N-methylanilide in 40 ml of dimethylacetamide. The ice bath is removed 10 minutes later and the solution is stirred overnight at room temperature. Thereupon 11.2 g (19.6 millimoles) of 2,4,6-triiodo-5-amino-isophthalic-acid-monomethylamide is introduced; a slight heat of reaction is observed. After 20 hours, the brown solution is stirred into 200 ml of water. The precipitate is evacuated some time later, thoroughly stirred with 200 ml of water, evacuated and dried. This raw product (26 g) is dissolved in 130 ml of ethanol, reacted with 10.9 ml (55.6 millimoles) of dicyclohexylamine and stirred overnight. The crystallized salt is evacuated, after-rinsed with fresh ethanol, suspended in 260 ml of water and reacted with 7.6 ml (83.5 millimoles) of 11 N soda lye. The dicyclohexylamine is separated (6.2 ml), the aqueous solution is filtered through a moist, double folded filter, treated with charcoal, and acidified with 15.3 ml (184 millimoles) of 12 N hydrochloric acid. After stirring overnight, the precipitate is evacuated, thoroughly stirred with 240 ml of water, and dried.

Yield: 15.2 g (61.2% of theoretical) of the title compound. M.p. from 207° C. (decomposition). Iodine, computed=60.1%; measured=59.6%.

EXAMPLE 14

Decane-diacid-1-(3-carboxy-2,4,6-triiodo-anilide)-10-(3-carboxy-5-N-methylcarbamoyl-2,4,6-triiodo-anilide)

Similarly to example 3, an incomplete solution of 14.0 g (20 millimoles) of sebacic-acid-mono-2,4,6-triiodo-3-carboxy-anilide in 40 ml dimethylacetamide is reacted with 3.2 ml (44 millimoles) of thionyl chloride and then with 11.2 g (19.6 millimoles) of 2,4,6-triiodo-5-amino-isophthalic-acid-monomethylamide, and processed. After purification by means of the dicyclohexylamine salt, one obtains 15.8 g (83.5% of theoretical) of the title compound. M.P.=230°-240° C. (decomposition).

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of the formula

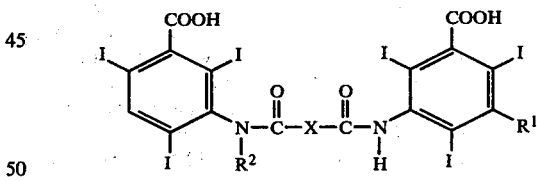

wherein
X is $C_{1-12}$-alkylene optionally interrupted by 1–4 oxygen atoms;
$R^1$ is —NH—$C_{2-4}$-alkanoyl, —$CH_2NH$—$C_{2-4}$-alkanoyl, in both of which alkanoyl can optionally be substituted by 1 or 2 hydroxy or $C_{1-4}$ alkoxy groups, or —$CONHR^3$, wherein $R^3$ is hydrogen, $C_{1-4}$ alkyl or $C_{1-5}$ alkyl substituted by 1–4 hydroxy or $C_{1-4}$-alkoxy groups;
$R^2$ is hydrogen or $C_{1-4}$ alkyl;
or a physiologically compatible salt thereof with an inorganic or organic base.
2. A compound of claim 1 wherein R' is —$CONHR^3$.
3. A compound of claim 1 wherein R' is —NH-alkanoyl.
4. A compound of claim 1 wherein R' is —$CH_2$—NH-alkanoyl.

5. A compound of claim 1 wherein the alkanoyl group in R' is acetyl, propionyl, hydroxyacetyl or α-hydroxypropionyl.

6. A compound of claim 1 wherein $R^3$ is H, methyl, ethyl, hydroxyethyl or 1,3-dihydroxy-propyl-(2).

7. Hexane-diacid-1-(3-carboxy-2,4,6-triiodo-anilide)-6-(3-carboxy-5-N-methyl-carbamoyl-2,4,6-triiodo-anilide), a compound of claim 1.

8. 3-oxapentane-diacid-1-(3-carboxy-2,4,6-triiodo-N-methylanilide)-5-(3-carboxy-5-N-methylcarbamoyl-2,4,6-triiodo-anilide), a compound of claim 1.

9. 3,6,9-trioxaundecane-diacid-1-(3-carboxy-2,4,6-triiodo-anilide)-11-(5-acetamido-3-carboxy-2,4,6-triiodo-anilide), a compound of claim 1.

10. An x-ray contrast medium comprising an amount of a compound of claim 1 effective as an x-ray contrast agent and a pharmaceutically acceptable carrier.

11. An x-ray contrast medium of claim 10 where the concentration of x-ray contrast agent is 50–400 mg I/ml.

12. A method of visualizing a part of the body comprising administering an effective amount of a compound of claim 1 and then subjecting the part of the body to x-ray diagnosis.

13. A method of claim 12 which is cholegraphy, liver visualization or computer tomography.

14. A method of claim 12 which is computer tomography of the liver.

* * * * *